(12) United States Patent
Morimoto et al.

(10) Patent No.: US 9,381,515 B2
(45) Date of Patent: Jul. 5, 2016

(54) CONTAINER FOR MEASURING CELL POTENTIAL

(75) Inventors: Shinji Morimoto, Osaka (JP); Yui Hagiwara, Osaka (JP)

(73) Assignees: Nipro Corporation, Osaka (JP); ReproCELL Incorporated, Kanagawa (JP)

( * ) Notice: Subject to any disclaimer, the term of this patent is extended or adjusted under 35 U.S.C. 154(b) by 235 days.

(21) Appl. No.: 13/386,568

(22) PCT Filed: Jul. 23, 2010

(86) PCT No.: PCT/JP2010/062421
§ 371 (c)(1),
(2), (4) Date: Jan. 23, 2012

(87) PCT Pub. No.: WO2011/010720
PCT Pub. Date: Jan. 27, 2011

(65) Prior Publication Data
US 2012/0119750 A1 May 17, 2012

(30) Foreign Application Priority Data
Jul. 24, 2009 (JP) .................... 2009-173015

(51) Int. Cl.
*G01R 29/12* (2006.01)
*B01L 3/00* (2006.01)

(52) U.S. Cl.
CPC ....... *B01L 3/5085* (2013.01); *B01L 2300/0645* (2013.01); *B01L 2300/0829* (2013.01)

(58) Field of Classification Search
CPC .............................. B01L 3/5085; G01R 29/12
USPC ............ 324/450, 458, 515, 691–692; 435/29
See application file for complete search history.

(56) References Cited

U.S. PATENT DOCUMENTS 6,315,940 B1 * 11/2001 Nisch et al. ................. 435/287.1
6,977,722 B2   12/2005 Wohlstadter et al.
(Continued)

FOREIGN PATENT DOCUMENTS

JP    2007124971 A    5/2007
WO    02055653 A1    7/2002
(Continued)

OTHER PUBLICATIONS

Catalog of QT-Screen, automated measurement system for high-throughput QT prolongation, made by Multi Channel Systems, issued by Bio Research Center Co., Ltd., www.brck.co.jp/MCS/qtscreencataloguejpl.pdf and partial English translation, 2007, 5 pages.

(Continued)

*Primary Examiner* — Arleen M Vazquez
*Assistant Examiner* — Brent J Andrews
(74) *Attorney, Agent, or Firm* — The Webb Law Firm

(57) ABSTRACT

A cellular electric potential measuring container includes a container body and an electrode substrate, the electrode substrate being attached to a lower end of the container body so as to form a plurality of wells. The container body is made from resin and comprises a plurality of tubular portions whose upper and lower ends are open, each of the tubular portions comprises in an inner cavity a measurement portion tapered toward the lower end and having a measurement hole at the lower end, and further on an inner wall at least two retaining means retaining the measurement portion. The electrode substrate comprises a substrate body, with a plurality of measurement electrodes and a plurality of reference electrodes being disposed on one surface of the substrate body. The container body is attached to the surface of the substrate body on which the measurement electrodes and the reference electrodes are disposed, such that the measurement electrodes are exposed through the measurement holes.

4 Claims, 4 Drawing Sheets

(56) References Cited

U.S. PATENT DOCUMENTS

| | | |
|---|---|---|
| 2003/0113833 A1 | 6/2003 | Oka et al. |
| 2005/0279634 A1* | 12/2005 | Ozaki et al. ............... 204/556 |
| 2009/0081765 A1 | 3/2009 | Nakatani et al. |
| 2010/0019756 A1 | 1/2010 | Hiraoka et al. |
| 2010/0019782 A1* | 1/2010 | Watanabe et al. ............ 324/692 |
| 2010/0304423 A1* | 12/2010 | Asai et al. ..................... 435/29 |

FOREIGN PATENT DOCUMENTS

| | | |
|---|---|---|
| WO | 2007001091 A1 | 1/2007 |
| WO | 2007119772 A1 | 10/2007 |
| WO | 2007132769 A1 | 11/2007 |
| WO | 2009038079 A1 | 3/2009 |

OTHER PUBLICATIONS

Catalog, "QT-Screen, Automated Cardiac Electrophysiology for Drug Profiling and Safety Screening" by Multi Channel Systems, 6 pages.

Saito, Michiyoshi et al., "ES Cells for Drug Discovery and Screening Business", Gekkan Medical Science Digest (2007), vol. 33, No. 14, pp. 1272-1275 and 1295.

\* cited by examiner

CONTAINER FOR MEASURING CELL POTENTIAL

TECHNICAL FIELD

The present invention relates to a cellular electric potential measuring container for measuring cellular electric potential after being mounted on an electric potential measuring device.

BACKGROUND ART

In current new drug development, it is necessary to discover the toxicity caused by a drug at an early stage. One known example of this toxicity is drug-induced (acquired) QT prolongation syndrome, which is a disease that causes severe arrhythmia in a patient.

Drug-induced QT prolongation syndrome is a serious disease with which QT interval prolongation appears on an electrocardiogram after drug administration, and ventricular fibrillation often occurs after TdP (Torsades de pointes: non-sustained polymorphic ventricular tachycardia), resulting in syncope or sudden death. In fact, out of the 25 drugs whose sales were stopped in the US market after 1980, five drugs have been determined as causing drug-induced QT prolongation syndrome.

In this regard, to discover toxicity that is caused by a drug, non-patent literature 1 discloses a measurement method in which the effect of a drug on the activity of an ion channel is analyzed based on the change in the electric potential of a cell in a drug-administered culture solution. This measurement method is carried out once a cellular electric potential measuring container is mounted on an electric potential measuring device. This cellular electric potential measuring container includes a plurality of wells for accommodating a culture solution and cells, and a measurement electrode and a reference electrode are disposed on the bottom of each well.

However, with the cellular electric potential measuring container of non-patent literature 1, it is sometimes difficult to obtain accurate measurement results by bringing a cell into contact with a fine measurement electrode.

PRIOR ART DOCUMENTS

Non-Patent Documents

Non-Patent Document 1: URL: http://www.brck.co.jp/MCS/qtscreencataloguejp1.pdf

SUMMARY OF INVENTION

An object of the present invention is to provide a cellular electric potential measuring container with which an accurate measurement result can be readily obtained by bringing a cell into contact with a fine measurement electrode in cellular electric potential measurement using a cellular electric potential measuring container.

To achieve the above-described object, the present invention provides a cellular electric potential measuring container comprising a container body and an electrode substrate, the electrode substrate being attached to a lower end of the container body so as to form a plurality of wells, the cellular electric potential measuring container being for measuring cellular electric potential after being mounted on an electric potential measuring device and, wherein the container body is made from resin and comprises a plurality of tubular portions whose upper and lower ends are open, each of the tubular portions comprises: in an inner cavity a measurement portion tapered toward the lower end and having a measurement hole at the lower end, and further on an inner wall at least two retaining means retaining the measurement portion, the electrode substrate comprises a substrate body, with a plurality of measurement electrodes and a plurality of reference electrodes being disposed on one surface of the substrate body, and the container body is attached to the surface of the substrate body on which the measurement electrodes and the reference electrodes are disposed, such that the measurement electrodes are respectively exposed through the measurement holes.

The cellular electric potential measuring container of the present invention is a disposable component that is used in a system for measuring a change of cellular electric potential that occurs in response to a plurality of new drug candidate compounds in wells. The cellular electric potential measuring container of the present invention is used after being mounted on a dedicated electric potential measuring device (not shown in figures). The configuration thereof includes a plurality of wells. The wells are formed by attaching an electrode substrate to the lower end of a container body. That is, the container body serves as the side wall of the wells, and the electrode substrate serves as the bottom of the wells. The formed wells are fluid tight such that a medium used in a measurement (usually a culture solution) can be accommodated. Both a measurement electrode and a reference electrode are disposed on the bottom of each well. Thereby, the cellular electric potential can be measured in each well. The term "cell" as used herein should be understood to encompass not only a single cell but also cell mass (spheroid) formed by aggregation of a plurality of cells.

The cellular electric potential measuring container of the present invention is disposable as stated above. Therefore, to attain an inexpensive product, at least the container body is entirely made from resin. The resin is not particularly limited in the present invention as long as the resin can be molded into the container body and is electrically insulating. Specific examples of the resin include polypropylene, polystyrene, polyester, polycarbonate, and the like. In particular, from the viewpoint of low material cost, high transparency, and good appearance, the resin is preferably polystyrene. A method for producing the container body is not necessarily limited as long as the container body is readily produced, but given the complex structure of the container body, it is usually desirable to produce the container body by injection molding.

The container body includes tubular portions that serve as the side wall of each well. The upper and lower ends of the tubular portions are open. The upper end is open to accommodate a cell and a medium (usually a culture solution) when carrying out a measurement, and the lower end is open to allow the electrode substrate, which will be described later, to serve as a bottom. The shape of the tubular portions is not particularly limited in the present invention, but it is desirably cylindrical from the viewpoint of easy production.

The inner cavities of the tubular portions on the container body are each provided with a measurement portion. The measurement portion has a structure tapered toward the lower end, and has a measurement hole at the lower end. This tapered structure is a structure for allowing a cell to move to the measurement hole by its own weight. Moreover, the measurement hole is to expose the measurement electrode of the electrode substrate, which will be described later. That is, a cell placed in the measurement portion can move all the way to the measurement hole at the lower end due to the tapered structure of the measurement portion and by its own weight. And, since the measurement electrode is exposed through the measurement hole, the cell can come into contact with the measurement electrode. The shape of the measurement portion is not necessarily limited in the present invention, but from the viewpoint of allowing a cell to readily move to the measurement hole of the measurement portion, it is desirable that at least the tapered structure portion is circular in a planar view from the upper end of the tubular portion.

The measurement portion is retained by at least two retaining means. The container body is made from resin, and deformation occurs elsewhere in the container body upon molding the container body, and therefore it has been difficult to expose the measurement electrode, which will be described later, through the measurement hole of the measurement portion in all the wells. However, in the present invention, the number of retaining means retaining the measurement portion is at least two. That is, at least two points of the measurement portion are retained, thus enabling the measurement electrode, which will be described later, to be successfully exposed through the measurement hole of the measurement portion. If only one retaining means is provided, or if only one point is retained, due to the deformation of resin (for example, the retaining means itself or the tubular portion), a portion where the measurement electrode, which will be described later, is not exposed through the measurement hole of the measurement portion is created. As long as the retaining means has strength sufficient to prevent the measurement portion from falling off the tubular portion, the shape and other features thereof are not particularly limited. The retaining means is not particularly limited as long as the number thereof is at least two, but it is desirable that the retaining means are arranged in places where the measurement hole (the measurement electrode, which will be described later) serves as the point of symmetry in a planar view from the upper end of the tubular portion such that the measurement portion can be more evenly retained. From the viewpoint of being able to nearly perfectly position the measurement hole and easy production, the number of the retaining means is most preferably four.

Meanwhile, the electrode substrate includes a substrate body, and a plurality of measurement electrodes and a plurality of reference electrodes are disposed on one surface of the substrate body.

The substrate body is composed of a, so-called, electrically insulating material. Examples of the material include polypropylene, polystyrene, polyester, fluororesin, polycarbonate, acrylic resin, paper phenol, paper epoxy, glass composites such as glass epoxy, alumina, and the like. From the viewpoint of high conductivity, high mechanical strength, and low cost, in general, glass epoxy is often selected. However, the present invention is not limited by these materials for the substrate body.

The measurement electrode is an electrode that comes into contact with a cell and measures the ion channel activity of the cell as electric potential, and the reference electrode is an electrode that comes into contact with a medium used in a measurement (usually a culture solution) and measures electric potential that is regarded as, so-called, reference electric potential. The measurement electrode and the reference electrode are disposed in places such that one measurement electrode and one reference electrode are present on the bottom of each well when the electrode substrate is attached to the container body and wells are thus formed. On the bottom of each well, the measurement electrode is disposed in a place where a cell can come into contact, or that is, a place where the measurement electrode is exposed through a measurement hole of the container body when the container body is attached to the electrode substrate. On the other hand, there is no particular limitation on the reference electrode if the reference electrode on the bottom of each well is disposed in a place where a cell does not come into contact, or that is, a place where the reference electrode is not exposed through a measurement hole of the container body when the container body is attached to the electrode substrate. As a matter of course, the measurement electrode and the reference electrode on the bottom of each well are not electrically connected. Examples of materials for the measurement electrode and the reference electrode include gold, silver, carbon, platinum, ruthenium oxide, palladium, and the like. In particular, gold is suitably used from the viewpoint of high electric conductivity, but the present invention is not limited by these electrode materials. The measurement electrode and the reference electrode can be suitably constructed according to a technique such as screen printing, ink jet, sputtering, or vapor deposition. Therefore, the present invention is also not limited by these electrode constructing methods.

A method for attachment of the container body to the electrode substrate is not particularly limited in the present invention. For example, as in conventional cellular electric potential measuring containers, attachment may be performed using an adhesive.

Moreover, the present invention also provides a cellular electric potential measuring container including a plurality of tubular portions arranged such that space is provided therebetween and a bridging portion provided between adjacent tubular portions. Accordingly, each of the tubular portions does not deform, and thus the measurement electrode is more accurately exposed through the measurement hole of the measurement portion in each tubular portion. As long as the bridging portion has strength sufficient to prevent the tubular portions from being separated apart, the shape and other features thereof are not particularly limited.

Effects of Invention

According to the cellular electric potential measuring container of the present invention, it is easy to obtain an accurate measurement result by bringing a cell into contact with a fine measurement electrode.

DETAILED DESCRIPTION OF THE INVENTION

Hereinbelow, embodiments of the present invention will be described using the figures, but the present invention is not construed as being limited to the embodiments described later.

Figure 1:
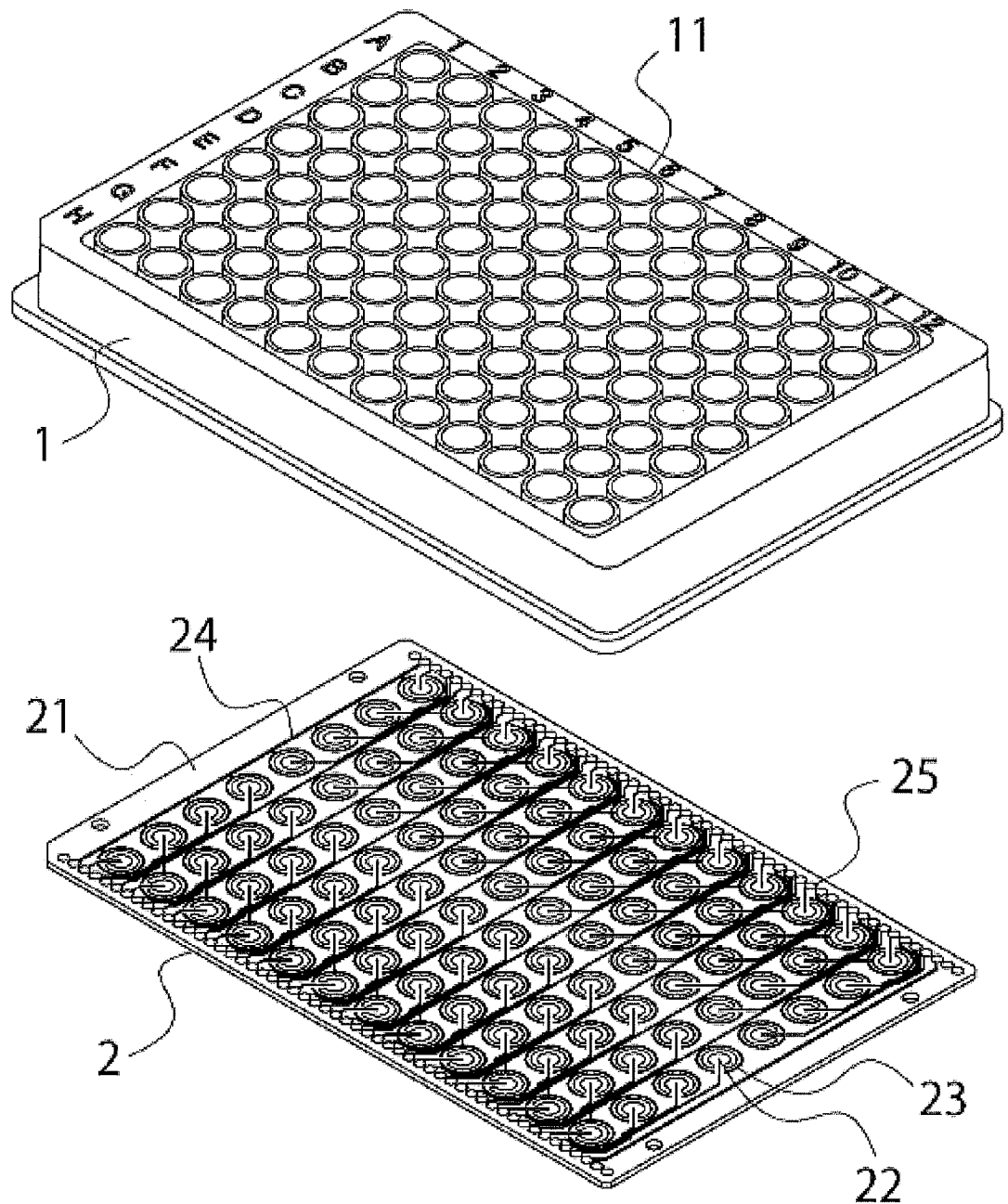
FIG. 1 is an exploded perspective view of the cellular electric potential measuring container of the present invention.

FIG. 1 is an exploded perspective view of the cellular electric potential measuring container of the present invention. The cellular electric potential measuring container of the present invention is primarily composed of a container body 1 and an electrode substrate 2. The container body 1, which is made from resin, includes a plurality of tubular portions 11 having a cylindrical shape whose upper and lower ends are open. The structure of the inner cavity of each tubular portion 11 will be described later. Each tubular portion 11 constitutes the side wall of a well.

Meanwhile, the electrode substrate 2 forms the bottom of the wells. The electrode substrate 2 includes a substrate body 21 composed of an electrically insulating material, and a plurality of measurement electrodes 22 and reference electrodes 23 are disposed on the substrate body 21. A measurement electrode 22 of the electrode substrate 2 in FIG. 1 is disposed substantially at the center of a reference electrode 23 that has a C shape. The measurement electrode 22 has such a fine structure that it is not clearly visible in FIG. 1, and thus a detailed description is given in reference to FIG. 2. All of the measurement electrodes 22 and reference electrodes 23 are lead by lead wires 24 that are independent of each other to connectors 25 arranged in line along one side of the electrode substrate. A reason that the reference electrodes 23 are C-shaped is to secure space for disposing lead wires to lead the measurement electrodes 22 to the connectors 25. Although not shown, the connectors 25 are also disposed on the opposite surface of the electrode substrate 2 (the surface on which no measurement electrodes 22 or reference electrodes 23 are disposed). When the cellular electric potential measuring container of the present invention is mounted on a dedicated electric potential measuring device (not shown), the connectors 25 on the opposite surface of the electrode substrate 2 are electrically connected to the dedicated electric potential measuring device, thus enabling cellular electric potential to be measured.

Figure 2:
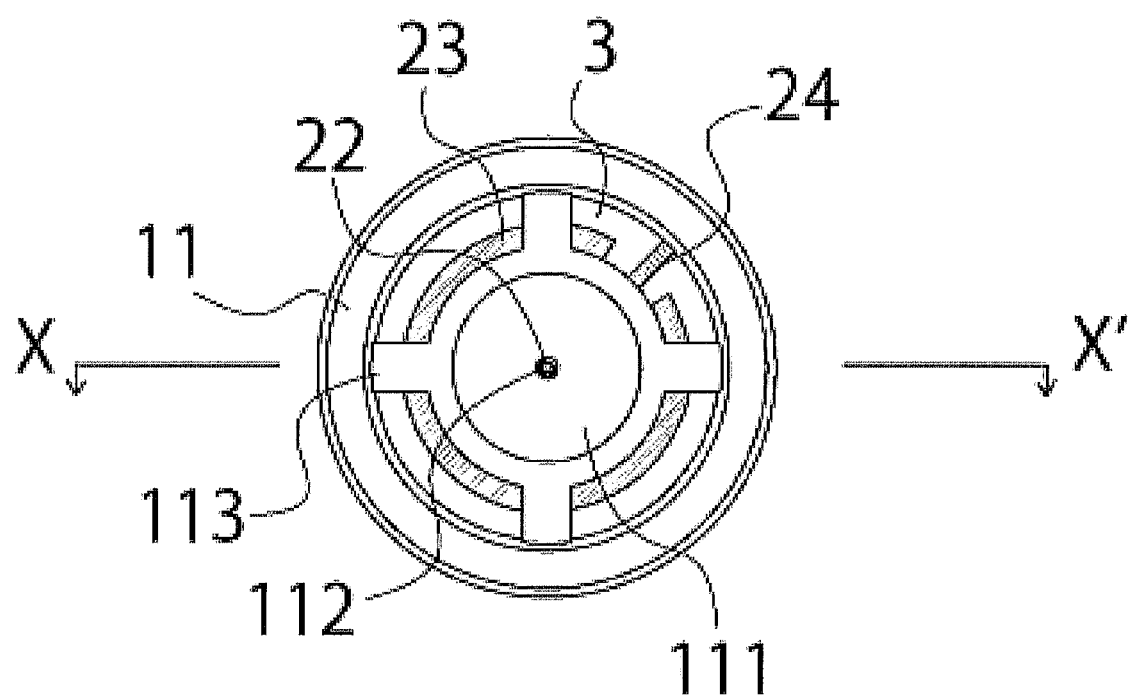
FIG. 2 is a top view of a well of the cellular electric potential measuring container of the present invention.

FIG. 2 is a top view of one well 3 of the cellular electric potential measuring container of the present invention. For the well 3, the tubular portion 11 of the container body 1 serves as a side wall, and the electrode substrate 2 serves as a bottom. The measurement electrode 22 and the reference electrode 23 are disposed on the bottom of each well 3. The tubular portion 11 that serves as the side wall of the well 3 is provided with a measurement portion 111 having a circular measurement hole 112 and four retaining means 113. The measurement electrode 22 having a fine structure is exposed through the measurement hole 112. Since the present invention has at least two retaining means 113 (four in FIG. 2), the measurement electrode 22 is accurately exposed. If only one retaining means 113 is provided, it is difficult to expose the measurement electrode 22 through the measurement hole 112 in all the wells 3 due to the deformation of the retaining means 113 and the tubular portion 11 or the like. On the other hand, the reference electrode 23 is exposed at the periphery of the measuring portion 111 on the bottom of the well 3.

Figure 3:
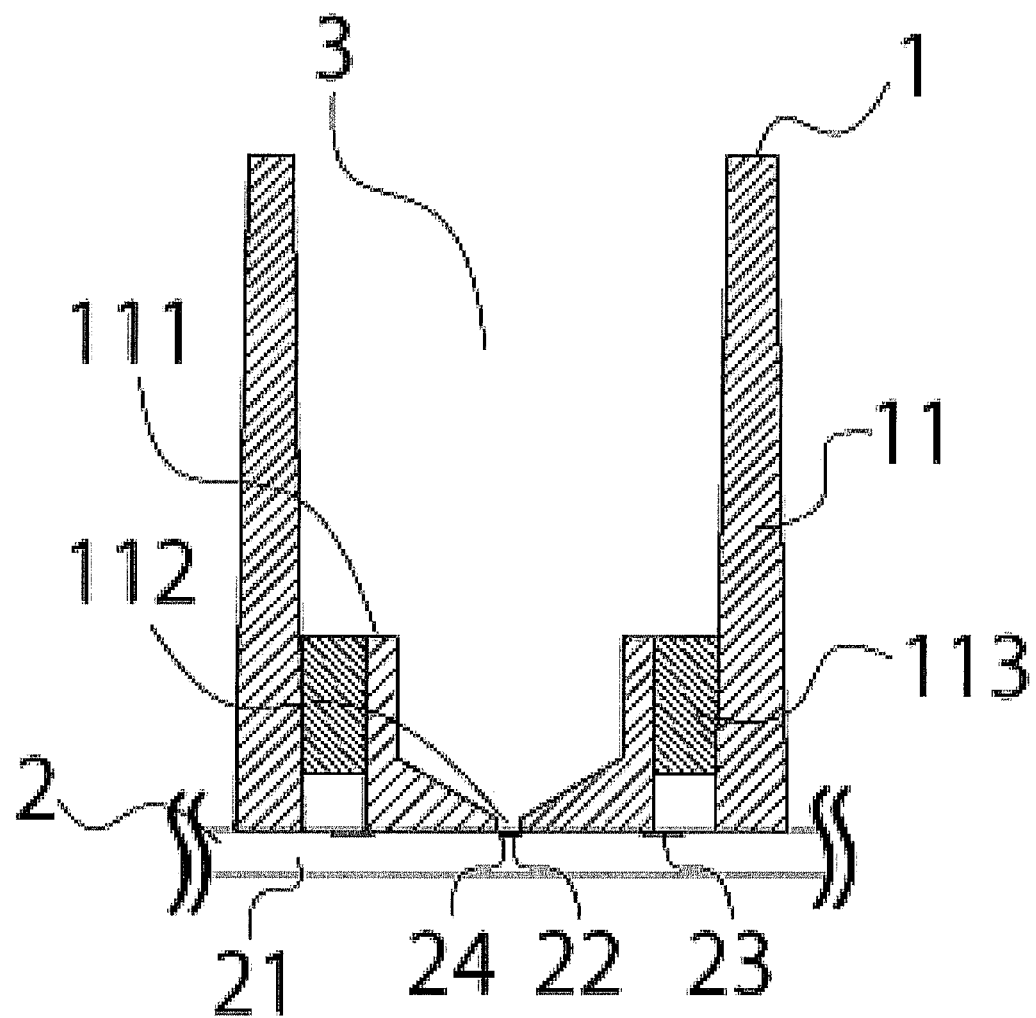
FIG. 3 is a cross-sectional view of a well of the cellular electric potential measuring container of the present invention (cross section taken along the X-X' in FIG. 2).

The structure of one well 3 of the cellular electric potential measuring container of the present invention will now be further described. FIG. 3 is a cross-sectional view of one well 3. The cross-sectional view of FIG. 3 shows the cross section taken along the line X-X' in FIG. 2. The measurement portion 111 has a structure tapered toward the lower end of the well 3 (tubular portion 11), i.e., toward the measurement hole 112. This structure allows a cell placed in the measurement portion 111 to move to the measurement hole 112 by its own weight and to come into contact with the measurement electrode 22 exposed through the measurement hole 112.

Figure 4:
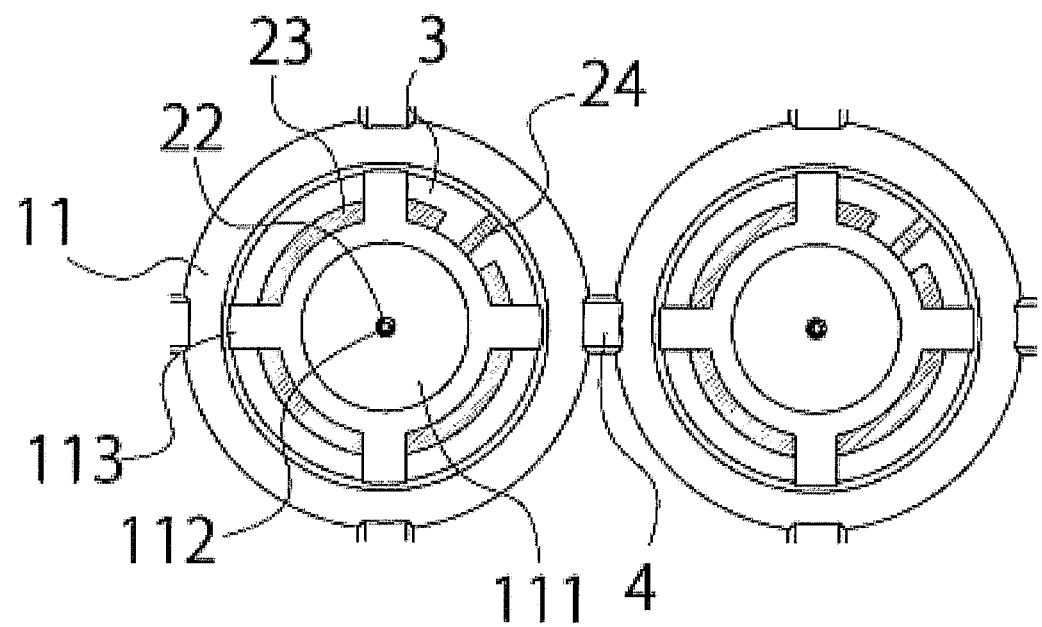
FIG. 4 is a top view of two adjacent wells of the cellular electric potential measuring container of the present invention.

FIG. 4 shows a desirable configuration of the cellular electric potential measuring container of the present invention, and is a top view of two adjacent wells 3. While the wells 3 are arranged such that space is provided therebetween, the wells 3 are connected to each other via a bridging portion 4. In other words, two adjacent wells 3 are indirectly connected via a bridging portion 4. If adjacent wells 3 (tubular portions 11) are in direct contact, it is likely that sink mark is generated at the point of contact, and the measurement hole 112 on the bottom of the well 3 fails to be correctly positioned. Also, if no bridging portion 4 is present, it is likely that deformation of the tubular portion 11 occurs, and the measurement hole 112 on the bottom of the well 3 fails to be correctly positioned.

A method for measuring cellular electric potential using the cellular electric potential measuring container of the present invention is performed in a manner nearly comparable to a method that uses a conventional cellular electric potential measuring container. However, a method that uses the cellular electric potential measuring container of the present invention is different from conventional methods in that a cell is placed in the measurement portion 111. A cell placed in the measurement portion 111 moves to the measurement hole 112 due to the tapered structure of the measurement portion 111 and by its own weight and can come into contact with the measurement electrode 22 exposed through the measurement hole 112.

The present invention enables an accurate measurement of cellular electric potential, and therefore the present invention achieves rapid drug screening and will contribute to new drug development.

The invention claimed is:

1. A cellular electric potential measuring container comprising a container body and an electrode substrate, the electrode substrate being attached to a lower end of the container body so as to form a plurality of wells, wherein
   the container body is made from resin and comprises a plurality of tubular portions whose upper and lower ends are open,
   each of the tubular portions comprises:
      in an inner cavity a measurement portion tapered toward the lower end and having a measurement hole at the lower end, and further
      on an inner wall at least two retaining means retaining the measurement portion,
   the electrode substrate comprises a substrate body, with a plurality of measurement electrodes and a plurality of reference electrodes
   the container body is attached to a side of the substrate body on which the measurement electrodes and the reference electrodes are disposed, such that the measurement electrodes are respectively exposed through measurement holes,
   each of the reference electrodes is exposed at a periphery of the measurement portion on a bottom of one of the plurality of wells,
   a place where each of the measurement electrodes is exposed is where a cell comes into contact with the measurement electrode, and
   the place where each of the measurement electrodes is exposed is disposed on a same side of the substrate body as a place where each of the reference electrodes is exposed.

2. The cellular potential measuring container of claim 1, wherein the tubular portions are arranged such that space is provided therebetween, and a bridging portion is provided between adjacent tubular portions.

3. The cellular potential measuring container of claim 1, wherein the measurement electrode is disposed substantially at the center of the reference electrode which has a C shape.

4. The cellular potential measuring container of claim 1, wherein when the container body is attached to the electrode substrate, the measurement electrode is exposed through the measurement hole of the container body and the reference electrode is not exposed through the measurement hole of the container body.

* * * * *